(12) United States Patent
Goetz et al.

(10) Patent No.: US 10,967,087 B2
(45) Date of Patent: *Apr. 6, 2021

(54) STERILIZER WITH A HUMIDITY CONTROL SYSTEM

(71) Applicant: 3M INNOVATIVE PROPERTIES COMPANY, Saint Paul, MN (US)

(72) Inventors: Jay R. Goetz, Deephaven, MN (US); Sherman L. Bartz, Saint Paul, MN (US); Barry W. Robole, Woodville, MN (US)

(73) Assignee: 3M Innovative Properties Company, St. Paul, MN (US)

(*) Notice: Subject to any disclaimer, the term of this patent is extended or adjusted under 35 U.S.C. 154(b) by 263 days.

This patent is subject to a terminal disclaimer.

(21) Appl. No.: 16/160,412

(22) Filed: Oct. 15, 2018

(65) Prior Publication Data

US 2019/0046677 A1 Feb. 14, 2019

Related U.S. Application Data

(63) Continuation of application No. 15/102,321, filed as application No. PCT/US2014/069647 on Dec. 11, 2014, now Pat. No. 10,130,728.

(Continued)

(51) Int. Cl.
*A61L 2/24* (2006.01)
*A61L 2/20* (2006.01)

(52) U.S. Cl.
CPC .............. *A61L 2/24* (2013.01); *A61L 2/206* (2013.01); *A61L 2202/14* (2013.01)

(58) Field of Classification Search
CPC .......... A61L 2/24; A61L 2/20; A61L 2202/14; A61L 2/206
See application file for complete search history.

(56) References Cited

U.S. PATENT DOCUMENTS

| | | |
|---|---|---|
| 3,687,612 A | 8/1972 | Ernst |
| 3,936,270 A | 2/1976 | Gunther |
| 4,098,573 A | 7/1978 | Gunther |
| 4,203,943 A | 5/1980 | Gillis |
| 4,457,892 A | 7/1984 | Young |
| 4,843,867 A | 7/1989 | Cummings |
| 5,082,636 A | 1/1992 | Andersen |

(Continued)

FOREIGN PATENT DOCUMENTS

| | | |
|---|---|---|
| CA | 2437711 | 8/2002 |
| CN | 102363045 | 2/2012 |

(Continued)

OTHER PUBLICATIONS

Brazil Search Report for BR112016013745-0.

(Continued)

*Primary Examiner* — Kevin Joyner
(74) *Attorney, Agent, or Firm* — Qiang Han

(57) ABSTRACT

The disclosed sterilizer includes a humidity control system for controlling humidity. The sterilizer for sterilizing objects comprises a chamber for receiving objects to be sterilized and a humidity control system. The humidity control system comprises a water control system which can be connected to a water source for injecting a first quantity of water vapor into the chamber, a pressure sensor in fluid communication with the chamber for measuring pressure in the chamber, a humidity sensor in fluid communication, or in selective fluid communication, with the chamber for sensing a first humidity value ($RH_{chamber}$) of the first quantity of water vapor in the chamber; and a controller configured to inject a second quantity of water vapor into the chamber.

11 Claims, 8 Drawing Sheets

Related U.S. Application Data

(60) Provisional application No. 61/916,439, filed on Dec. 16, 2013.

(56) References Cited

U.S. PATENT DOCUMENTS

| | | | |
|---|---|---|---|
| 5,344,622 | A | 9/1994 | Faddis |
| 5,445,792 | A | 8/1995 | Rickloff |
| 5,641,455 | A | 6/1997 | Rosenlund |
| 6,077,480 | A | 6/2000 | Edwards |
| 2002/0152792 | A1 | 10/2002 | Wang |
| 2007/0292305 | A1 | 12/2007 | Dempsey |

FOREIGN PATENT DOCUMENTS

| | | |
|---|---|---|
| CN | 102385399 A | 3/2012 |
| CN | 202740444 | 2/2013 |
| CN | 203070123 U | 7/2013 |
| EP | 914139 | 12/1962 |
| EP | 0016888 | 10/1980 |
| EP | 1682828 | 7/2006 |
| JP | H04-20345 | 1/1992 |
| JP | H05-016491 | 1/1993 |
| JP | H05-016491 A | 1/1993 |
| KR | 10-2011-0069472 | 6/2011 |
| WO | WO 1997-29789 | 8/1997 |
| WO | WO 1998-00176 | 1/1998 |
| WO | WO 2010/104948 | 9/2010 |
| WO | WO 2010/133842 | 11/2010 |

OTHER PUBLICATIONS

International Search report for PCT International Application No. PCT/US2014/069647 dated on Mar. 10, 2015, 3 pages.
China National Intellectual Property Administration Search Report dated May 20, 2020, for Application No. 201811122299.2, filed Dec. 11, 2014.

STERILIZER WITH A HUMIDITY CONTROL SYSTEM

CROSS REFERENCE TO RELATED APPLICATIONS

This application is a continuation of U.S. application Ser. No. 15/102,321, filed Jun. 7, 2016, which is a national stage filing under 35 U.S.C. 371 of PCT/US2014/069647, filed Dec. 11, 2014, which claims priority from U.S. Provisional Application Ser. No. 61/916,439, filed Dec. 16, 2013, the disclosure of which is incorporated by reference in its/their entirety herein.

FIELD

The present disclosure generally relates to systems and methods for controlling humidity in a closed chamber, and particularly to systems (e.g., sterilizers) and methods for sterilizing objects with biocidal gas that include systems and methods for controlling humidity in a sterilizing chamber.

BACKGROUND

Goods that cannot withstand autoclaving temperatures can be sterilized with sterilizers using a biocidal gas such as ethylene oxide. Ethylene oxide sterilizers have a sterilizing chamber where the goods to be sterilized can be placed. The door of the sterilizing chamber can then be sealed, and the operator can initiate a sterilizing cycle. For ethylene oxide to exert maximum effect, the goods can be pre-treated with the proper amount of humidity; to achieve this, a vacuum (e.g., partial vacuum) can be drawn within the sterilizing chamber and then water can be released into the chamber. When the correct amount of humidification has been achieved within the chamber, an appropriate charge of ethylene oxide gas can be released and allowed to act on the surfaces and be absorbed by the goods for a period of time. Once the goods are sterile, the ethylene oxide gas can be purged from the chamber and the goods, and the chamber door can be released so the goods can be unloaded.

It can be desirable to achieve the proper humidification within the chamber, i.e., prior to releasing the ethylene oxide gas, at a relatively quick rate, ideally without over-humidifying the chamber, which may require premature chamber evacuation and/or disrupt an entire sterilization cycle.

SUMMARY

In some sterilizing systems, the sterilization, or "biocidal," gas (e.g., ethylene oxide) employed can have a deleterious effect on the humidity sensor. Such a sensor is present in conventional sterilizers in order to ensure that the goods have been pretreated to an appropriate level of humidity for the ethylene oxide to have its full effect. The humidity generally preconditions any microorganisms present to make the sterilizing gas more efficacious. As a result, various sterilization standards may require a particular level of humidity be maintained (e.g., for a prescribed period of time) in a sterilizing chamber prior to release of the sterilizing gas.

The reactive nature of the biocidal gas can damage the relatively delicate humidity sensor, causing it to fail. When this occurs, the apparatus can fail safely, i.e. the damaged sensor indicates that the appropriate level of humidity has not been reached, and as a result, the sterilizing gas can be prevented from being released. However, the failure can result in an inconvenient disruption to an overall protocol. As a result, in some cases, a sterilizer design can be employed which protects components (e.g., humidity sensors) which are sensitive to the effects of the biocidal gas.

For example, U.S. Pat. No. 5,641,455 (Rosenlund et al.), which is incorporated herein by reference, describes a sterilizer that includes a humidity sensor connected to a vacuum line at a point removed from or outside of the sterilizing chamber, and an isolation valve connected to the vacuum line at a point between the sterilizing chamber and the humidity sensor. However, in such systems, humidification of the chamber to a desired level can be slow and/or tedious, because discrete humidity measurements are taken at various timepoints during a humidification cycle, where a sample of the atmosphere in the chamber is removed and positioned in contact with the humidity sensor, rather than constantly monitoring the humidity level of the chamber. Based on the humidity of the sample, the quantity and/or timing of the next water injection can be determined. Systems and methods of the present disclosure employ a control system and process that utilizes constant pressure monitoring of the atmosphere within the chamber for ratiometrically calculating the next water injection quantity. The systems and methods of the present disclosure can account for load size (e.g., in terms of chamber pressure drop as a result of load absorption). As a result, the systems and methods of the present disclosure can achieve and/or maintain a desired humidity level within the sterilizing chamber more efficiently.

The systems and methods of the present disclosure can also be extended to non-sterilizing systems and methods for ratiometrically controlling relative humidity in a closed chamber, based on pressure measurements and humidity measurements of the atmosphere (i.e., gaseous environment) within the chamber. Some non-sterilizing applications or systems in which the humidity control systems and methods of the present disclosure can be employed include, but are not limited to, incubators, safes, refrigerators, environmental test chambers, humidors, or any other suitable application or system.

Some aspects of the present disclosure provide a method for controlling humidity. The method can include providing a chamber configured to receive objects to be sterilized; injecting a first quantity of water into the chamber as water vapor; determining a pressure rise and a pressure drop in the chamber resulting from injecting a first quantity of water into the chamber; calculating an absorption ratio (AR) as the ratio of the pressure drop to the pressure rise; sensing the humidity of the chamber after injecting a first quantity of water to determine a first humidity value ($RH_{chamber}$); comparing the first humidity value to a pre-selected humidity value ($RH_{setpoint}$) to determine a humidity error ($RH_{error}$), wherein $RH_{error} = RH_{setpoint} - RH_{chamber}$; and injecting a second quantity of water into the chamber as water vapor, wherein the second quantity of water is calculated based on the absorption ratio (AR) and the humidity error ($RH_{error}$).

Some aspects of the present disclosure provide a sterilizer for sterilizing objects with biocidal gas. The sterilizer can include a chamber for receiving objects to be sterilized, and a biocidal gas control system, which can be connected to a biocidal gas source for controlling the release of biocidal gas into the chamber. The sterilizer can further include a humidity control system for manipulating the gaseous environment within the chamber. The humidity control system can include a water control system which can be connected to a water source for injecting a selectable quantity of water into the chamber; a pressure sensor in fluid communication with the chamber for measuring pressure in the chamber; and a humidity sensor in fluid communication, or in selective fluid communication, with the chamber for sensing a humidity value ($RH_{chamber}$) of the gaseous environment in the chamber. The humidity control system can further include a controller configured to: (i) determine a pressure drop and a pressure rise in the chamber resulting from a first quantity of water injected into the chamber, (ii) calculate an absorption ratio (AR) as the ratio of the pressure drop to the pressure rise, (iii) compare the humidity value ($RH_{chamber}$) to a pre-selected humidity value ($RH_{setpoint}$) to determine a humidity error ($RH_{error}$), wherein $RH_{error}=RH_{setpoint}-RH_{chamber}$, and (iv) determine a second quantity of water to be injected into the chamber based on the absorption ratio (AR) and the humidity error ($RH_{error}$).

Some aspects of the present disclosure provide a humidity control system for manipulating the gaseous environment within a chamber. The system can include a water control system which can be connected to a water source for injecting a selectable quantity of water into the chamber; a pressure sensor in fluid communication with the chamber for measuring pressure in the chamber; and a humidity sensor in fluid communication, or in selective fluid communication, with the chamber for sensing a humidity value ($RH_{chamber}$) of the gaseous environment in the chamber. The humidity control system can further include a controller configured to: (i) determine a pressure drop and a pressure rise in the chamber resulting from a first quantity of water injected into the chamber, (ii) calculate an absorption ratio (AR) as the ratio of the pressure drop to the pressure rise, (iii) compare the humidity value ($RH_{chamber}$) to a pre-selected humidity value ($RH_{setpoint}$) to determine a humidity error ($RH_{error}$), wherein $RH_{error}=RH_{setpoint}-RH_{chamber}$, and (iv) determine a second quantity of water to be injected into the chamber based on the absorption ratio (AR) and the humidity error ($RH_{error}$).

Other features and aspects of the present disclosure will become apparent by consideration of the detailed description and accompanying drawings.

DETAILED DESCRIPTION

Figure 1:
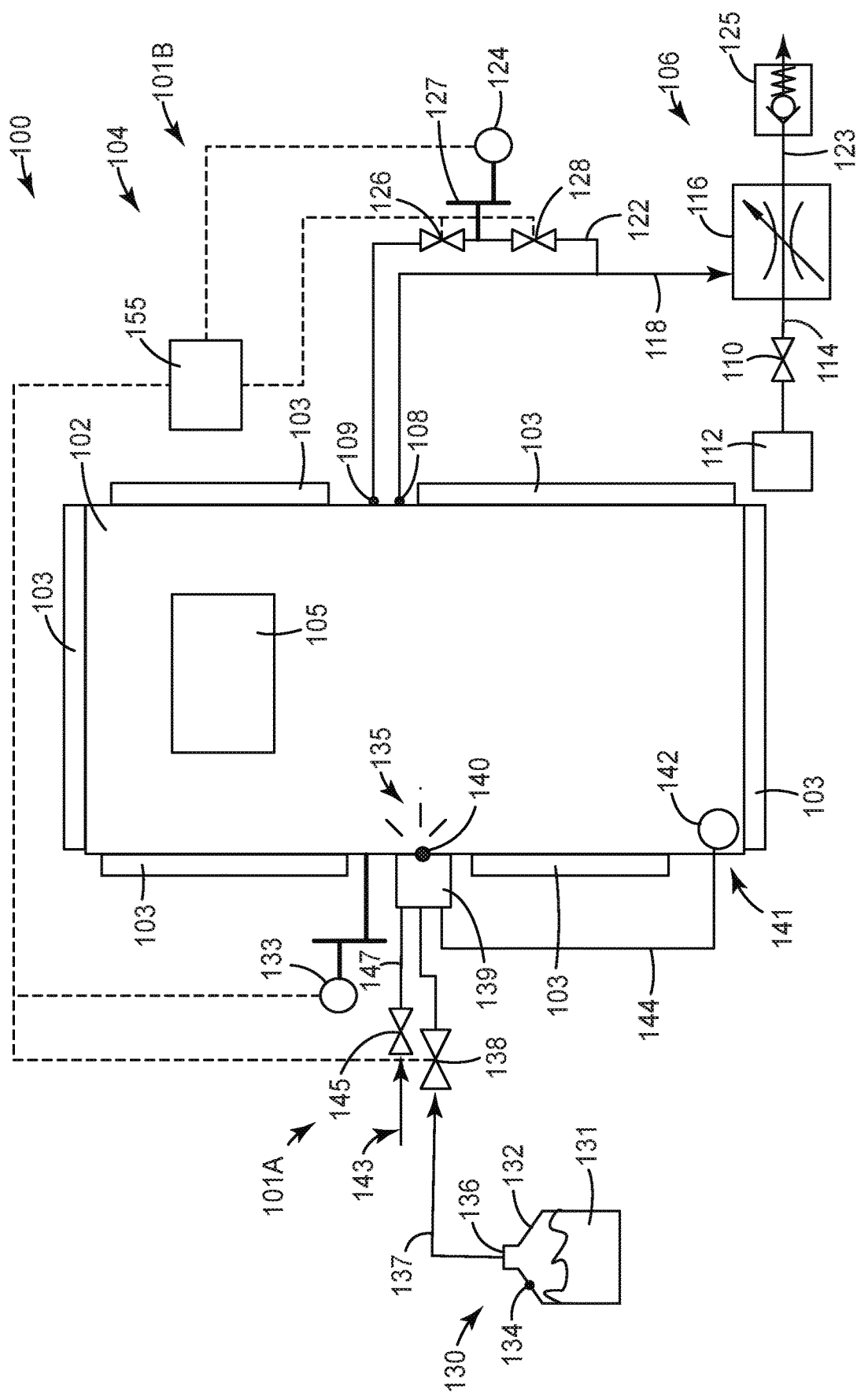
FIG. 1 is a schematic diagram of a sterilizer according to one embodiment of the present disclosure, the sterilizer comprising a humidity control system according to one embodiment of the present disclosure.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected," and "coupled" and variations thereof are used broadly and encompass both direct and indirect connections and couplings. It is to be understood that other embodiments may be utilized, and structural or logical changes may be made without departing from the scope of the present disclosure.

The present disclosure generally relates to systems and methods for controlling the amount of a gas of interest in a closed chamber, and particularly to systems and methods for controlling humidity in a closed environment (e.g., as part of a method of sterilizing objects with biocidal gas). Most particularly, the present disclosure relates to systems and methods for sterilizing objects with biocidal gas that include systems and methods for controlling humidity in a sterilizing chamber.

In general, systems and methods of the present disclosure include measuring chamber pressure during and after injection of a gas (e.g., water as steam) into the chamber. Such pressure measurements are used to define a pressure ratio (e.g., an absorption ratio) characteristic of a load present in the chamber, which can then be used to calculate an absorption coefficient. The pressure ratio and/or the absorption coefficient can then be incorporated as an input to a control algorithm for determining the subsequent quantity (e.g., volume) of gas to be injected to achieve or maintain a prescribed setpoint for that gas. The pressure ratio and/or the absorption coefficient can also be used as an input for an algorithm for determining the rate at which the next interrogation (e.g., humidity measurement) occurs.

The pressure ratio and/or the absorption coefficient can generally be used to represent and account for a load present in the chamber. A "load" generally refers to one or more objects configured to be positioned within the chamber, such that the load can be conditioned in the chamber. For example, with respect to sterilization systems and methods, the term "load" refers to one or more objects to be positioned and sterilized in the chamber.

Systems and methods of the present disclosure are able to dynamically adjust a process for delivering gas into a chamber—e.g., a humidification process—for a given load. For example, systems and methods of the present disclosure can generally provide a relatively small initial injection to determine a load response, which will be different for each load, each chamber, each system, etc. The load response can generally be characterized and accounted for by calculating a pressure ratio during and following initial and subsequent injections to determine an absorption ratio (AR) and/or an absorption coefficient (AC), calculations for which are described in greater detail below. Generally, smaller or less hygroscopic loads will have a smaller AR and AC (i.e., will absorb less), which is indicated by a flat or even slightly rising pressure during absorption time (i.e., following injection of a gas). Larger or more hygroscopic loads, on the other hand, will generally have a larger AR and AC, which is indicated by a generally decreasing pressure drop during absorption time.

Various parameters used in systems and methods of the present disclosure can be scaled or adjusted based on AR and/or AC. For example, during a ramp-up phase for achieving a desired level (i.e., setpoint) of a gas, injection time (i.e., injection quantity) of the gas for the next injection can be calculated based on (e.g., proportional to) the AR and/or AC resulting from one or more previous injections (e.g., the immediately preceding injection). In addition, after the chamber has achieved a desired level and is in a hold phase, absorption time (i.e., the amount of time allowed for a load positioned in the chamber to absorb the gas) can be calculated based on the AR and/or AC resulting from one or more previous injections (e.g., the immediately preceding injection).

It is generally true and can be a useful goal of the systems and methods of the present disclosure, that when AR is near zero (or AC is near 1—formulas are described below with respect to FIGS. 5, 6A and 6B), the load objects are at equilibrium with respect to the humidity environment inside the chamber. The present inventors discovered that AR (and/or AC) can be used to accelerate convergence of the chamber and the load (i.e., chamber+load) to an acceptable, stable target humidity.

As mentioned above, the systems and methods of the present disclosure can be used in sterilizers and sterilization methods, respectively, for sterilizing a load of objects, e.g., with a biocidal gas. FIG. 1 schematically illustrates a sterilizer 100 according to one embodiment of the present disclosure, which includes a humidity control system 101A, 101B according to one embodiment of the present disclosure.

As shown, the sterilizer 100 includes a sterilizing chamber 102 for holding a load 105 of objects to be sterilized. The chamber 102 comprises the volume capable of receiving goods, i.e., the load 105, to be sterilized.

The sterilizer 100 can include an overall control system 104 (which can include a controller 155, described in greater detail below, as well as additional control systems of the sterilizer 100) for manipulating the gaseous environment within the chamber 102. The chamber 102 can include a door (not shown) which can be opened to load or unload the load 105 from the chamber 102. The chamber 102 can also include one or more seals (e.g., employed with the door) for providing a gas tight environment within the chamber 102 but for the ports of the control system 104 as discussed below.

In some embodiments, it can be necessary to preheat the chamber 102 prior to introduction of the biocidal gas. In some embodiments, one or more heaters 103 can be located in thermal communication with the chamber 102. For example, as shown in FIG. 1, in some embodiments, the heaters 103 can surround the chamber 102.

In some embodiments, e.g., embodiments employing ethylene oxide gas as the biocidal gas, it can be necessary to subject the objects to be sterilized to a substantial partial vacuum (or air removal) as a pretreatment prior to introduction of the biocidal gas in order to assure complete penetration of the gas. This can be accomplished by a vacuum control system 106. The vacuum control system 106 is in fluid communication, or selective fluid communication, with the chamber 102 via one or more ports, such as ports 108 and 109. When it is desired to draw a vacuum in the chamber 102, vacuum pump valve 110 is activated, which allows pressurized air from air source 112 to flow through manifold 114 to venturi 116. Although a venturi system is depicted, one of ordinary skill in the art will recognize that a vacuum pump could alternatively be used to draw the vacuum and will understand that the venturi system is illustrated by way of example only. When venturi 116 is operated, a vacuum is drawn on line 118, and gas in the chamber 102 is withdrawn via port 108. A branch line 122 also connects to the chamber 102 through port 109. The exhaust from the venturi 116 is carried away through line 123, and through an exhaust outlet 125 to appropriate pollution abatement equipment.

The gas in branch line 122 is monitored by one or more humidity sensors 124. The flow of gas past humidity sensor 124 is conditional, based on the states of a first intake valve 126 (e.g., a humidity sensor isolation valve) and a second intake valve 128 (e.g., a humidity sensor check valve), collectively referred to as relative humidity (RH) sample valves 126, 128, or "RH sample valves" 126, 128.

In some embodiments, e.g., embodiments employing ethylene oxide gas as the biocidal gas, it can also be necessary to pre-condition the load 105 with the proper amount of humidity prior to the introduction of the biocidal gas. To accomplish this, the sterilizer 100 includes a humidity control system, which is illustrated as comprising two portions 101A and 101B in FIG. 1. Particularly, the humidity control system 101A, 101B can include a water control system 130 for injecting a selectable quantity of water into the chamber 102; one or more pressure sensors 133 (one is illustrated and described for simplicity) in fluid communication with the chamber 102 for measuring pressure in the chamber 102; the one or more humidity sensors 124 (one is illustrated and described for simplicity) in fluid communication, or in selective fluid communication via the RH sample valves 126, 128, with the chamber 102 for sensing a humidity value ($RH_{chamber}$) of the gaseous environment in the chamber 102; and a controller 155. In some embodiments, the vacuum control system 106 can also be considered to form a portion of the humidity control system 101A, 101B.

The controller 155 can be configured to acquire data from the pressure sensor 133 and the humidity sensor 124 (e.g., while allowing for various delays in data acquisition) and use this data to (i) calculate an absorption ratio (AR) (e.g., and ultimately, an absorption coefficient (AC)) for the load 105 based on the pressure drop and pressure rise experienced in the chamber 102 during and after injection of water, (ii) calculate a humidity error ($RH_{error}$) based on whether a desired humidity setpoint ($RH_{setpoint}$) has been achieved, and (iii) determine the amount of water to next be injected into the chamber 102 based on the absorption ratio (AR) (e.g., and the absorption coefficient (AC)) and the error ($RH_{error}$).

Generally, the controller 155 can be a suitable electronic device, such as, for example, a programmable logic controller ("PLC"), a microprocessor, a personal computer ("PC"), and/or other industrial/personal computing device. As such, the controller 155 may include both hardware and software components and is meant to broadly encompass the combination of such components. In addition, as represented by dashed lines in FIG. 1, the controller 155 can be connected to any other component of the humidity control system 101A, 101B (or other components of the sterilizer 100) via any combination of wired or wireless connections.

As mentioned above, in some embodiments, the sterilization gas can be deleterious to the humidity sensor 124. As a result, the humidity sensor can be located in a manifold (or "RH manifold") 127 outside of the chamber 102, with the first RH sample valve 126 (e.g., a solenoid valve) positioned to isolate the humidity sensor 124 from being in fluid communication with the chamber 102 (i.e., the first RH sample valve 126 is normally closed). As mentioned above, the humidity sensor 124 can be positioned between the first RH sample valve 126 and the second RH sample valve 128 (e.g., a solenoid valve) which can function as the RH exhaust valve and can be normally closed. The second RH sample valve 128 can be positioned between the humidity sensor 124 and the venturi 116 (or other vacuum pump system) of the vacuum control system 106, as shown in FIG. 1.

To sample the humidity of the chamber 102 during a humidification stage, both RH sample valves 126, 128 can be opened and the vacuum control system activated (e.g., the vacuum pump valve 110 opened and the venturi 116 is operational) to draw chamber air through the manifold 127.

The relative humidity (RH) level of air is dependent on temperature. At 38° C., the RH correction is approximately 3.2% RH/° C. and at 55° C., the RH correction is approximately 2.6% RH/° C. The temperature measured at the humidity sensor and the chamber temperature can be used to correct the humidity level measured during the humidification stage.

Conventional humidification or humidity control methods do not anticipate the amount of water being absorbed into the load 105 inside the chamber 102, which can vary widely depending on the size and contents of the load 105, which, in turn, can result in instability of humidity control. Such instability of humidity control can be at least partially attributed to a time lag in accurately sensing the humidity level of the chamber 102, e.g., in systems employing only humidity sensors, such as the humidity sensor 124 shown in FIG. 1, to control humidity. In embodiments in which the humidity sensor 124 is remote (as shown in FIG. 1), the time lag can be even greater as it includes the response time of the humidity sensor 124 (e.g., including the time to sample gaseous environment within the chamber 102). A remote humidity sensor 124 can affect the controllability of the process, because humidity is still changing when samples of the gaseous environment of the chamber 102 are being taken. As a result, the present inventors developed humidity control systems and methods that accurately estimate the effect of a first water injection as it is injected in order to determine an optimal injection quantity for a subsequent injection. In this case, an unbiased estimate can be created from the inner state of the control—i.e., the ability of the load 105 to absorb water.

The two portions 101A and 101B of the humidity control system are illustrated as being on opposite sides of the chamber 102 in FIG. 1 by way of illustration and example only, but it should be understood that this need not be the case.

With continued reference to the water control system 130 illustrated in FIG. 1, water 131 (e.g., distilled water) can be stored in water container 132, the water container having an air vent tube 134 to allow the water 131 in the water container 132 to be displaced, and a fill port 136. After a vacuum has been drawn in the chamber 102 and held for an appropriate time, water can then be introduced into the chamber 102 (e.g., in the form of steam), and a water inject valve 138 (e.g., a solenoid valve) can be opened. As shown by way of example only, the water inject valve 138 can be controlled by the controller 155. Water 131 from water container 132 then flows through line (or "water supply path") 137 into heater (or "heat sink", or "vaporization manifold") 139, where it is heated to form water vapor (i.e., steam) 135. The water vapor (i.e., steam) 135 enters the chamber 102 via port 140.

As the water vapor 135 enters the chamber 102 and is allowed to contact the load 105, and can be at least partially absorbed by the load 105. An absorption time or delay can be provided to allow sufficient time for load absorption of the water vapor 135. RH sample valves can then be opened, and a small amount of vacuum can be drawn through branch line 122 past humidity sensor 124, which monitors the humidity history of the objects in the chamber 102. Other aspects of humidity control methods used to achieve and maintain a desired humidity level will be described in greater detail below with reference to FIGS. 4, 5, 6A and 6B.

In general, injection of water into the chamber 102 relies on the pressure difference between the chamber (typically 160 mbar) and the ambient pressure outside the chamber (e.g., 980 mbar in St Paul, Minn.). To draw water from the ambient pressure water container 132 and inject it as water vapor 135 into the chamber 102, the heater 139 can be heated to a desired vaporization temperature (e.g., 95° C. when the pressure within the chamber is 160 millibar (mBar)). The water inject valve 138 in line 137 is used to control the length of time water vapor is injected into the chamber 102, thereby controlling the amount (e.g., volume) of water that is delivered into the heater 139, and ultimately, the amount (e.g., volume) of water vapor 135 that is injected into the chamber 102.

The vaporization of the water passing through the heater 139 can cool the heater 139. For this reason, it can be important not to unduely extend the maximum inject time for a given cycle to avoid cooling the heater 139 to a point where liquid water is injected into the chamber 102 and onto the load 105 being sterilized.

While the water control system 130 of the sterilizer 100 of FIG. 1 relies on a vacuum being drawn by the vacuum control system 106 to perform an injection, those of ordinary skill in the art will recognize that other types of injection can be employed, including injection provided by an external delivery device, such as a pump, a syringe, or another device suitable for injecting a controlled quantity.

When the objects are ready for the release of the biocidal gas, the RH sample valves 126, 128 can be closed to protect the vulnerable humidity sensor 124 from contact with the biocidal gas. When release of the biocidal gas is appropriate, a biocidal gas control system 141 can be employed to ensure that this is done safely, as described in U.S. Pat. No. 5,641,455 (Rosenlund et al.). The biocidal gas can be contained within a biocidal gas source 142, such as a receptacle (e.g., a sealed cartridge or canister), which can be located within the chamber 102. When release of the biocidal gas is desired, a series of events can be initiated to puncture or otherwise open the biocidal gas source 142. A desired quantity of biocidal gas then flows through line 144 into the heater 139, where it is heated to ensure that it is in a gaseous state. The biocidal gas then can enter the chamber 102 via the same port 140 as the water vapor 135, as illustrated, although this need not be the case.

Following exposure of the load 105 to the biocidal gas, it can be necessary to remove the gas from the chamber 102 and from the load 105 and to flush and aerate the chamber 102, as described in greater detail below. To accomplish flushing, the sterilizer 100 can employ the vacuum control system 106. To accomplish aeration, the sterilizer 100 can include an air intake control system 143, which can be used in conjunction with the vacuum control system 106. After a vacuum has been drawn in the chamber 102, an air valve 145 can be opened to allow filtered air (e.g., provided by drawing ambient air through a filter or filtration system) to flow through line 147, optionally through the heater 139 and into the chamber 102 via the same port 140 as the water vapor 135 and the biocidal gas. While the intake air is illustrated as entering the chamber 102 via the port 140, it should be understood that a separate port could be used for these purposes.

The timing of the various actuation events described in connection with the above description can be controlled by the controller 155. As a result, in some embodiments, the controller 155 may be considered to form a portion of the sterilizer 100 and/or the humidity control system 101A, 101B, or the controller 155 may be considered a separate component that works to control various actions or events pertaining to one or both of the sterilizer 100 as a whole and the humidity control system 101A, 101B.

Figure 2:
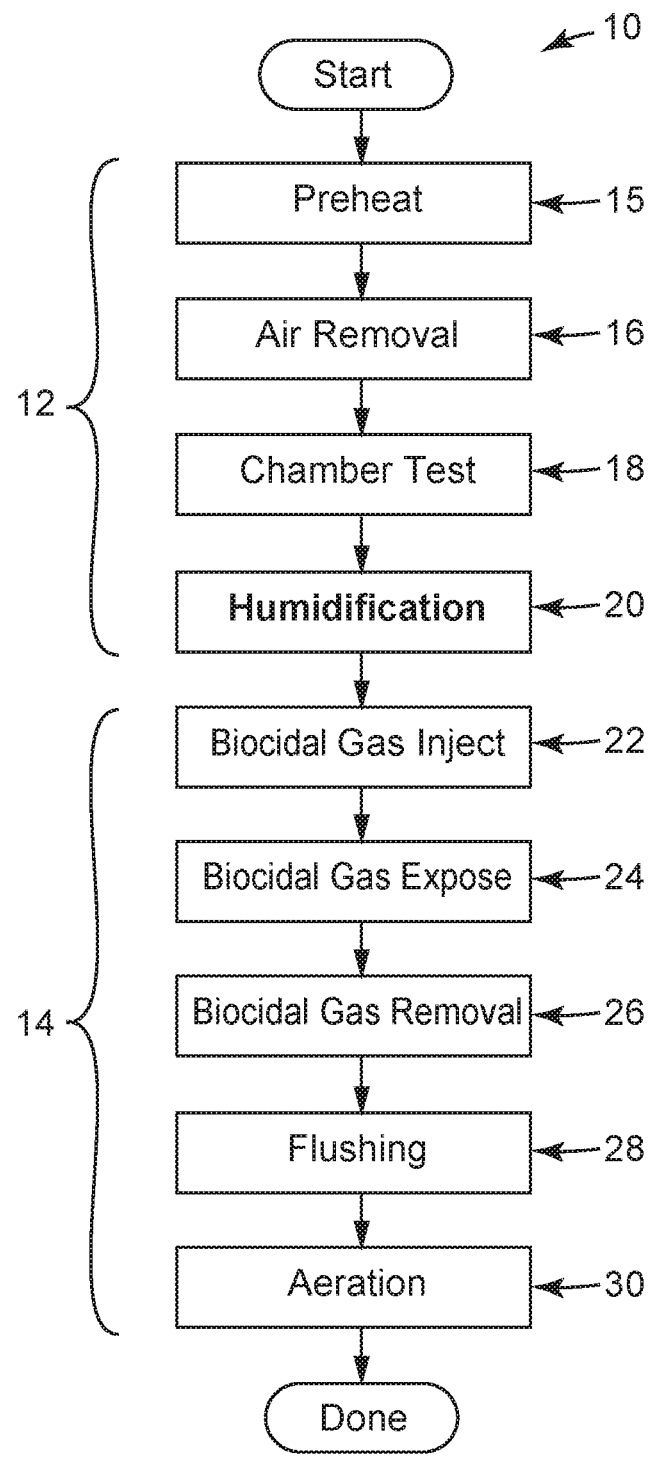
FIG. 2 is a flow chart for an overall sterilization process according to one embodiment of the present disclosure, where the overall sterilization process includes humidification.

FIG. 2 illustrates a flow chart for an exemplary overall sterilization process or cycle 10, which illustrates when humidification is performed, relative to other stages of the sterilization process 10. As shown in FIG. 2, a humidification stage 20 is a single component of the multistage sterilization process 10, which can be controlled by the controller 155. The sterilization process 10 will now be described with reference to the sterilizer 100 of FIG. 1.

The first four stages of the sterilization process 10 of FIG. 2 are referred to as the "conditioning phase" 12 of the sterilization process 10. The purpose of the conditioning phase is to ensure the load 105 to be sterilized is at the target temperature, pressure and relative humidity (RH) level prior to injecting gas (i.e., sterilizing gas) into the chamber. The final five stages of the sterilization process 10 are referred to as the "gas phase" 14 of the sterilization process 10.

A first preheat stage 15 heats the chamber 102 of FIG. 1 to the sterilization target temperature. The amount of time allowed to reach the target temperature is limited to ensure the heaters 103 are functioning properly. An error is reported and the process 10 is terminated if the chamber 102 does not reach the target cycle temperature within the specified amount of time. Also during the preheat stage, checks are made on the vacuum control system 106 used to pump down the chamber 102 to ensure that the venturi 116 can remove air from the chamber 102 and the chamber 102 can maintain a constant pressure. These checks are not necessary to heat the chamber 102 but can be performed at this early stage to avoid failures later in the process 10 due to a malfunctioning component. After exiting the preheat stage, the chamber temperature is controlled to the target temperature for the remainder of the sterilization process 10.

The sterilization process 10 can further include an air removal stage 16. The air removal stage 16 can use the vacuum control system 106 to pump-down (i.e. remove air from) the chamber 102. The amount of time allowed to reach the target cycle pressure is limited to ensure the sterilizer 100 is operating at the expected efficiency. An error is reported and the process 10 is terminated if the chamber 102 does not reach the target cycle pressure within the specified amount of time.

The sterilization process 10 can further include a chamber test stage 18. The chamber test stage 18 is responsible for testing the integrity of the chamber 102 by checking for a leak that could be a hazard if gas were present in the chamber 102. The chamber 102 is placed in the same state that it will be in prior to gas inject and the pressure is monitored for a specified amount of time. If the chamber leak rate (mbar/sec) is greater than the maximum amount allowed, an error is reported and the process 10 is terminated.

As mentioned above, the sterilization process 10 can further include the humidification stage 20. The humidification stage 20 is generally partitioned into two sequences: relative humidity (RH) ramp-up and RH hold. RH ramp-up is responsible for increasing the RH in the chamber 102 to the target, or setpoint, RH level ($RH_{setpoint}$). RH hold is responsible for maintaining the target RH level ($RH_{setpoint}$) for a specified amount of time to ensure the load 105 has sufficient time to absorb water vapor. The humidification stage 20, which includes humidity control methods of the present disclosure, is described in greater detail below with respect to FIGS. 3A-3C.

The sterilization process 10 can further include a biocidal gas inject stage 22. The biocidal gas inject stage 22 can include locking and/or sealing the chamber 102 and puncturing or otherwise opening the biocidal gas source 142 that contains the sterilization gas. As described above, the gas from the biocidal gas source 142 flows through the heater 139 (e.g., a manifold) heated to an appropriate temperature (e.g., 95° C. for ethylene oxide, in some embodiments) to ensure the gas is vaporized when entering the chamber 102. Generally, the pressure in the chamber 102 will increase due to the injection of the sterilization gas.

The sterilization process 10 can further include a biocidal gas expose stage 24. Following release of the biocidal gas into the chamber 102, the biocidal gas expose stage 24 can keep the chamber 102 closed (e.g., sealed) and can allow the load 105 to be exposed to the sterilization gas for the amount of time required to ensure the load will be sterilized.

The sterilization process 10 can further include a biocidal gas removal stage 26. The biocidal gas removal stage 26 can remove the biocidal gas in the chamber 102 that was not absorbed by the load 105 by using the vacuum control system 106 to again pump-down the chamber 102 to the target pressure for the given sterilization cycle. The chamber pressure prior to gas removal will be higher than the target pressure due to the pressure increase caused by injecting sterilization gas into the chamber 102.

The sterilization process 10 can further include a flushing stage 28. The flushing stage 28 again uses the vacuum control system 106 and opens (e.g., periodically) the air valve 152 to allow external air (e.g., which can be filtered) to enter the chamber 102 to remove the sterilization gas from the load 105. The on/off cycling of the air valve 152 is performed for a specified number of cycles. When these cycles are complete, the flushing stage 28 can further include locked aeration (e.g., if doors to the chamber 102 were locked prior to sterilization gas injection). In locked aeration, the venturi 116 can be on, and the air valve 152 can be open to allow external air (e.g., which can be filtered) to continuously flow into the chamber 102, while allowing chamber air to continuously flow out. Locked aeration can be performed for the amount of time required to ensure it is safe for an operator to remove the load 105 from the chamber 102. At the end of the flushing stage 28, the chamber 102 can remain closed with its doors unlocked.

The sterilization process 10 can further include an aeration stage 30. The aeration stage 30 continues where the flushing stage 28 left off (i.e., with the venturi 116 on and the air valve 152 open) except the chamber doors can now be opened. The duration of the aeration stage 30 can be configured by the user and can depend on the load sterilized, government regulations and other dependencies.

Details of the humidification stage 20 will now be described in greater detail with respect to FIGS. 3A, 3B and 3C. As shown, the humidification stage 20 includes a heat phase 40 (see FIG. 3A), a humidification ramp-up phase or mode 42 (see FIGS. 3A and 3B), and a humidification hold phase or mode 44 (see FIG. 3C). The heat phase 40 includes a first step 52 to ensure that chamber temperature control and heatsink (e.g., heater 139) temperature control are turned on.

A second step 56 checks to see if the heatsink is at its desired temperature. If not, the process proceeds to step 54. Step 54 checks to see if the heatsink has timed out. If not, the process returns to step 56. If so, an error 55 is reported indicating "Heatsink Timeout," and humidification is stopped. If in step 56 the heatsink was at its desired temperature, the process proceeds to an initialize step 58. At this step, the vacuum control system 106 is off (i.e., "Vacuum OFF"), the water control system 130 for injecting water is off (i.e., "Inject water OFF"), the RH sample valves 126, 128 are closed (i.e., "RH solenoids OFF"), and the air intake control system 143 is off and the air valve 145 is closed (i.e., "Vent CLOSED").

The process then proceeds to humidification ramp-up phase 42. At a first step 62, the humidity level within the chamber 102 ($RH_{chamber}$) is compared to a predetermined setpoint humidity ($RH_{setpoint}$). If $RH_{chamber}$ is at or above $RH_{setpoint}$, the process proceeds to the humidification hold phase 44 (see FIG. 3C). If $RH_{chamber}$ is not at or above $RH_{setpoint}$ (i.e., is below $RH_{setpoint}$), the process proceeds to step 64 to check to see if humidification timed out (e.g., as a result of failure of any of the humidity sensor 124, the water control system 130, the vacuum control system 106, etc.). If humidification timed out, an error 65 is reported indicating "Humidify Timeout," and humidification is stopped. If humidification did not time out, the process proceeds to a humidity control method or sequence 66, which generally includes water injection, time for the load 105 to absorb water, and humidity measurement. A humidity control method of the present disclosure is described in greater detail below with reference to FIGS. 4, 5, 6A and 6B.

Again, at step 68, the humidify timeout is checked. If humidification timed out, an error 67 is reported indicating "Humidify Timeout," and humidification is stopped. If humidification did not time out, the process proceeds to step 72 to check to see if water was injected during the humidity control method 66.

If water was injected during the humidity control method 66, the process proceeds to a recovery process 73. Particularly, the process proceeds to step 74 to check whether the heatsink (i.e., the heater 139) is at its desired temperature. If not, the process proceeds to step 76 to check to see if the heatsink has timed out. If so, an error 75 is reported indicating "Heatsink Timeout," and humidification is stopped. If the heatsink is at its desired temperature, the process cycles back to the beginning of the humidification ramp-up phase 42 (i.e., to step 62—see FIG. 3A) to check to see if $RH_{chamber}$ now meets or exceeds $RH_{setpoint}$, and so on.

If water was not injected during the humidity control method 66, the process cycles back to the beginning of the humidification ramp-up phase 42 (i.e., to step 62—see FIG. 3A) to check to see if $RH_{chamber}$ now meets or exceeds $RH_{setpoint}$, and so on.

Figure 3A:
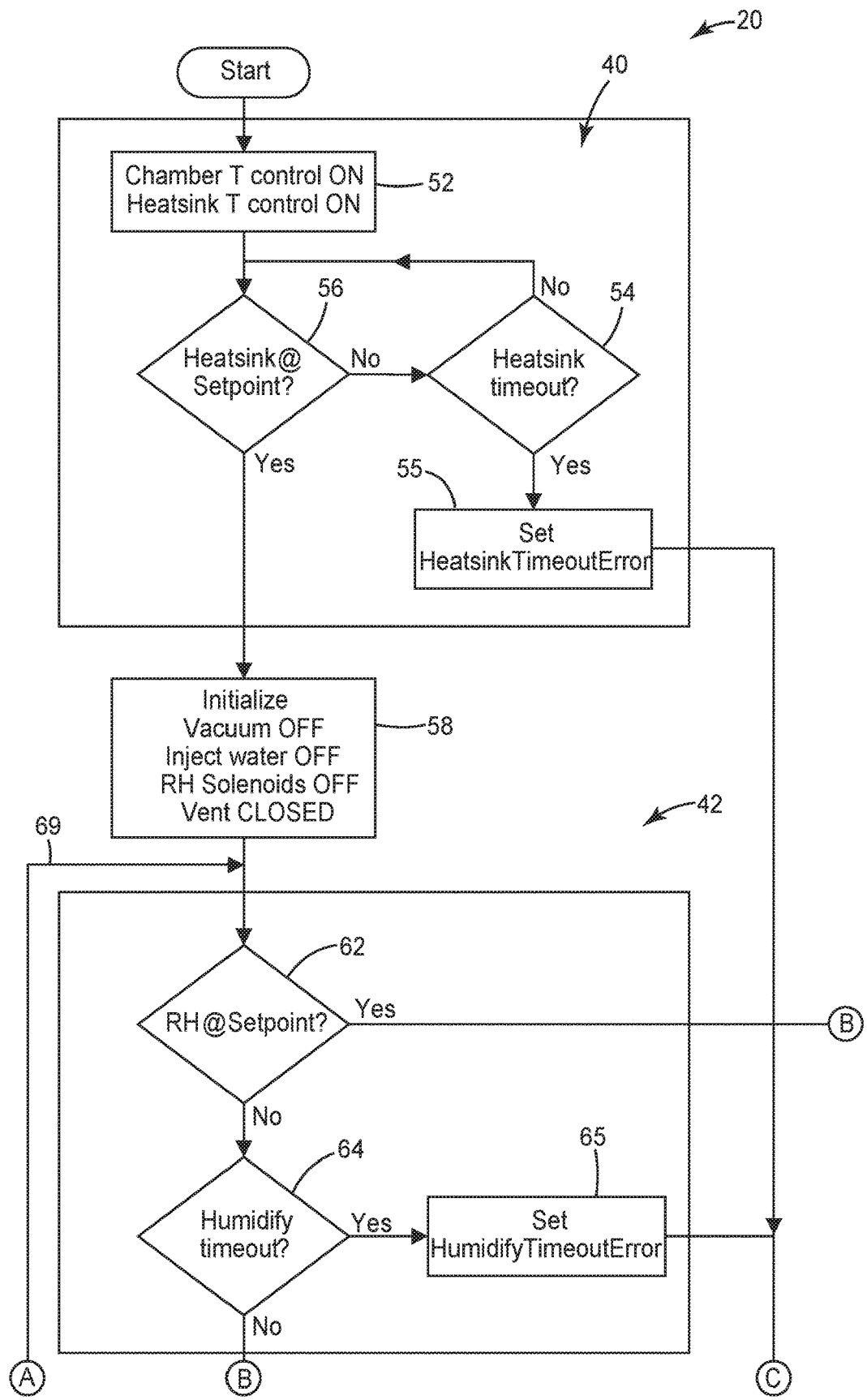
FIGS. 3A-3C illustrate a flow chart for an overall humidification process according to one embodiment of the present disclosure, incorporating a humidity control method represented in FIGS. 4, 5, 6A and 6B.
Figure 3B:
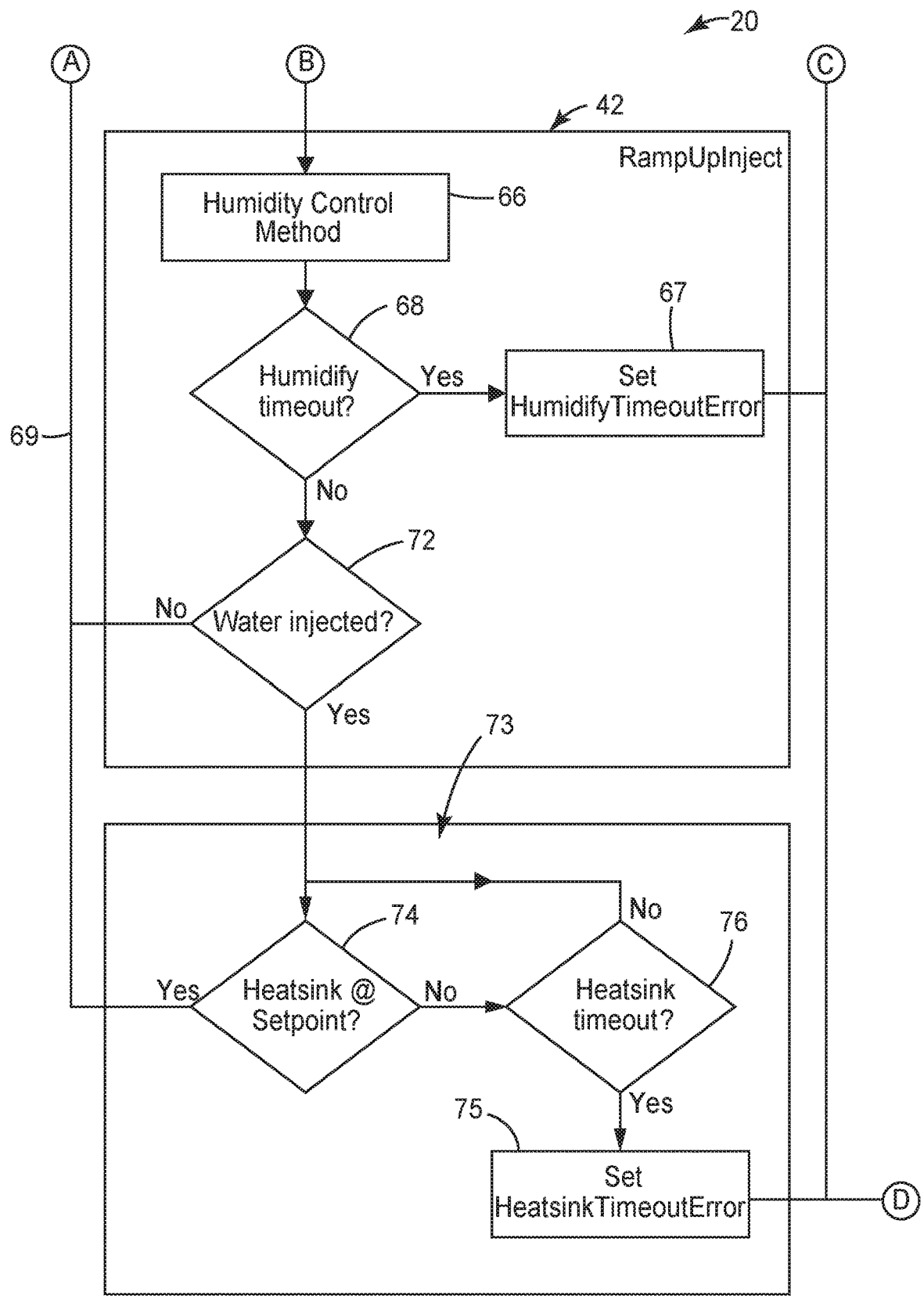
Figure 3C:
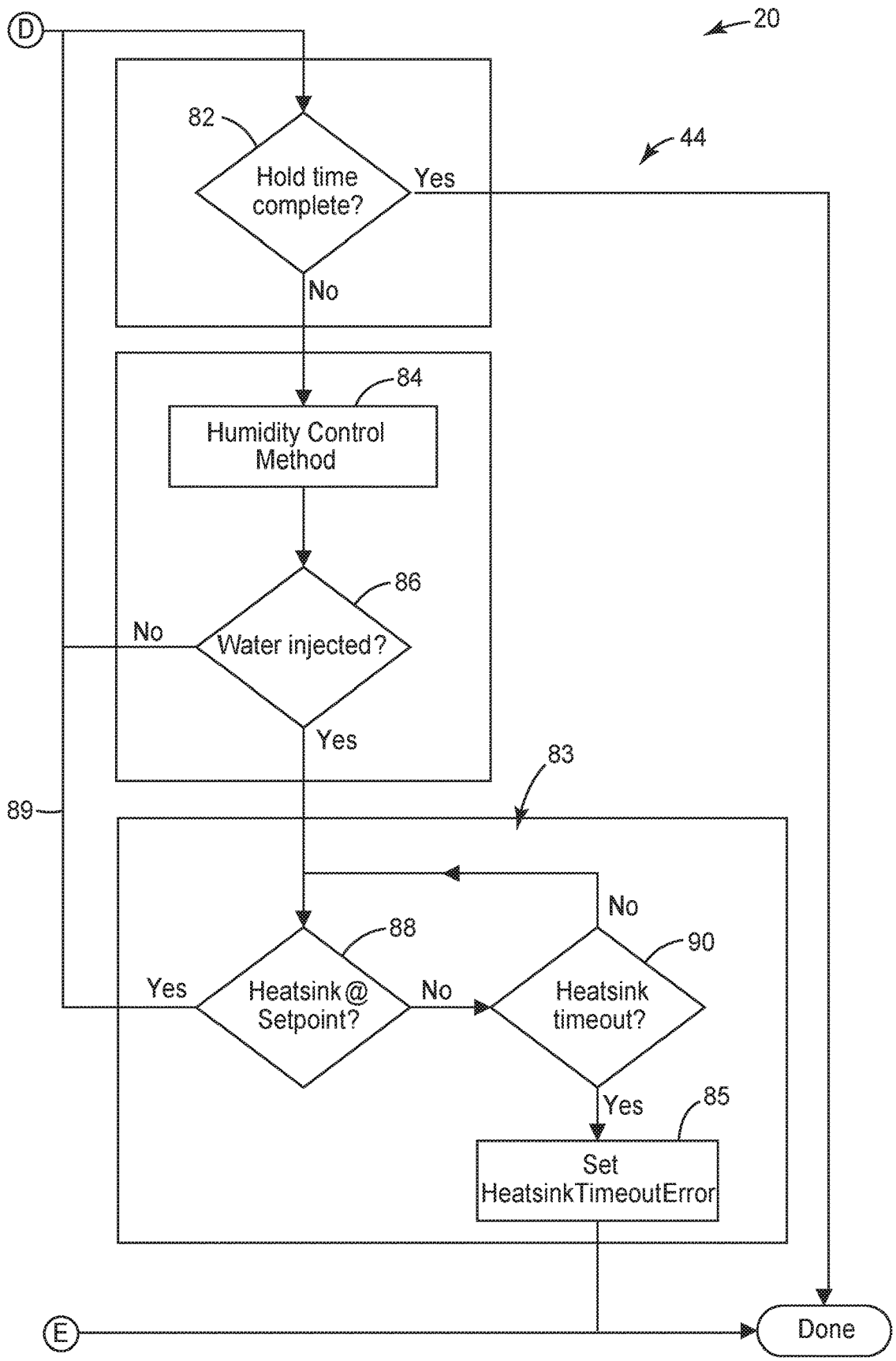

As shown in FIG. 3C, if $RH_{chamber}$ meets or exceeds $RH_{setpoint}$, the process proceeds to humidification hold phase 44. After $RH_{chamber}$ meets or exceeds $RH_{setpoint}$, the chamber 102 is held at this humidity level for a predetermined hold time, e.g., to ensure proper load absorption of the humidity. For example, in some embodiments, this hold time is about 30 minutes.

At step 82, the clock time is compared to the hold time. If the hold time is complete, the humidification stage 20 is complete. The sterilization process 10 (e.g., if the humidification is employed during a sterilization process for a sterilizer) can then proceed to the gas inject phase 22 (see FIG. 2).

If the hold time is not yet complete, the process proceeds to a humidity control method 84 for humidification hold (which can be the same, or essentially the same, control method as the humidity control method 66). The process then proceeds to step 86 to check to see if water was injected during the humidity control method 84.

If water was injected during the humidity control method 84, the process proceeds to a recovery process 83, which is similar to the recovery process 73 during the ramp-up phase 42. Particularly, the process proceeds to step 88 to check whether the heatsink (i.e., the heater 139) is at its desired temperature. If not, the process proceeds to step 90 to check to see if the heatsink has timed out. If so, an error 85 is reported indicating "Heatsink Timeout," and humidification is stopped. If the heatsink is at its desired temperature, the process cycles back to the beginning of the humidification hold phase 44 (i.e., to step 82) to check to see if the hold time is complete.

If water was not injected during the humidity control method 84, the process cycles back to the beginning of the humidification hold phase 44 (i.e., to step 82) to check to see if the hold time is complete, and so on.

Figure 4:
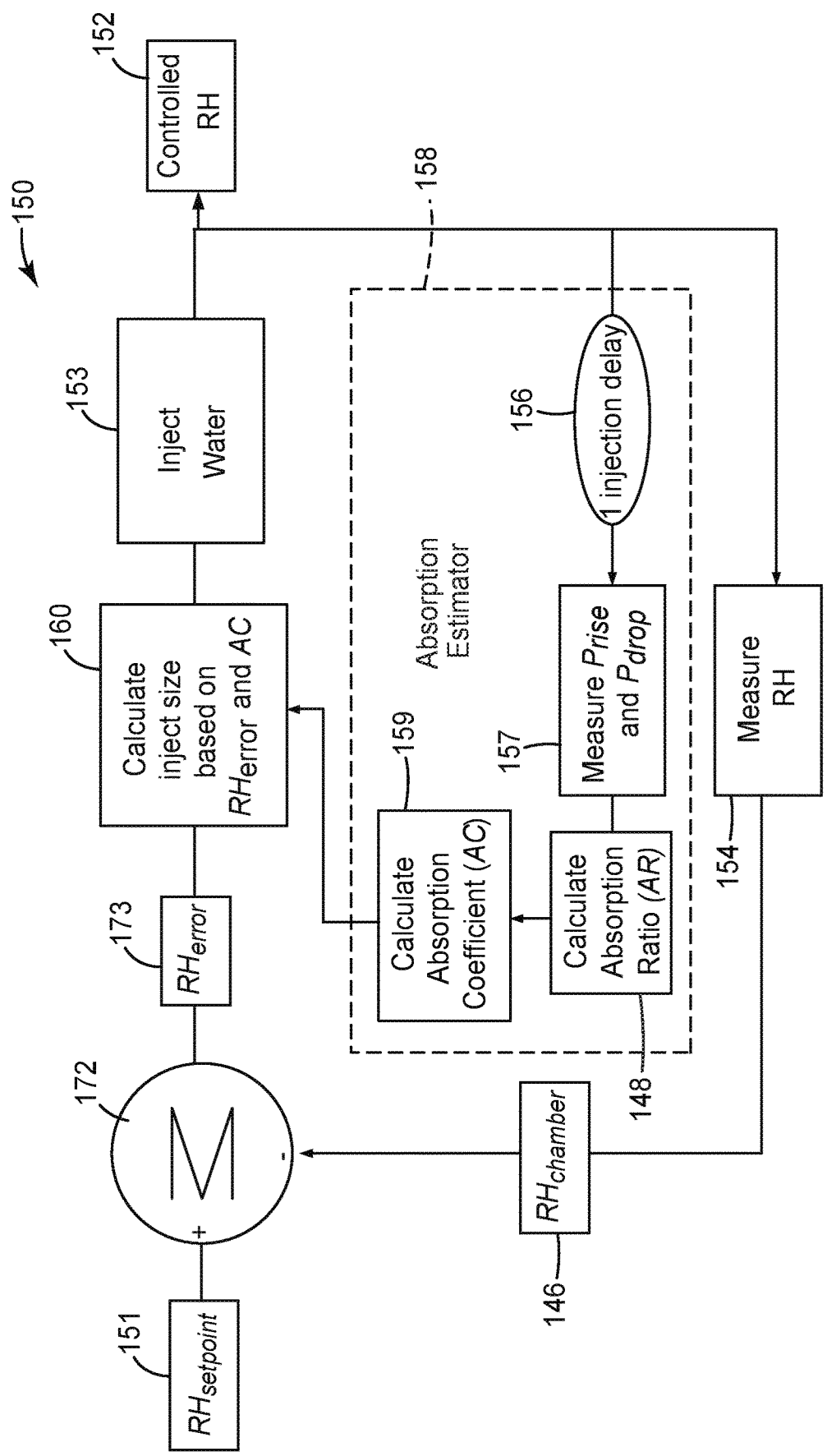
FIG. 4 is a control diagram representing a humidity control method according to one embodiment of the present disclosure.

The humidity control method (i.e., used at step 66 and 84 of the humidification stage 20 shown in FIGS. 3A-3C) will now be described in greater detail with respect to FIG. 4. FIG. 4 illustrates a humidity control method of the present disclosure in the form of a control loop diagram 150, where the input 151 is the desired humidity level for the chamber 102 ($RH_{setpoint}$), and the output 152 is controlled RH.

In some embodiments, $RH_{setpoint}$ can range from 10 to 90% RH, in some embodiments, from 20 to 80% RH, and in some embodiments, from 40 to 60% RH.

In general, the humidity control method includes injecting water vapor into the chamber 102 (represented by reference numeral 153 in FIG. 4), allowing time for the load 105 to absorb the water vapor, and then measuring the level of relative humidity (RH) present in the chamber 102 (represented by reference numeral 154 in FIG. 4). Measuring the level of RH present in the chamber 102 provides a value for $RH_{chamber}$ which then forms an input 146 to a summing junction 172, which provides an output 173 of $RH_{error}$, i.e., $RH_{error}=RH_{setpoint}-RH_{chamber}$. As a result, the injection time calculation is based on the chamber RH measurement (e.g., after the previous water injection), pressure measurements (e.g., sensed by the pressure sensor 133, e.g., during and after the previous water injection), and optionally chamber temperature (e.g., in the form of proportional gain constants).

Generally, a first quantity of water can be injected into the chamber 102, which can be constant, and the subsequent quantities of water to be injected can be calculated, e.g., based on data from the previous water injection. This is represented in FIG. 4 by the "1 injection delay" identified by reference numeral 156.

During and after the initial injection, pressure measurements can be made (e.g., using the pressure sensor 133 of FIG. 1) to determine a pressure rise ($P_{rise}$) and a pressure drop ($P_{drop}$), resulting from the first quantity of water that was injected. This is represented by reference numeral 157 in FIG. 4. These additional pressure measurements are used to estimate the effectiveness of the water injection on the relative humidity in the chamber 102 and thus act as an observer or estimator in the humidity control method. Specifically, the "absorption estimator" 158 is illustrated in the control diagram of FIG. 4.

As mentioned above, an absorption ratio (AR) can be calculated as the ratio of the pressure drop ($P_{drop}$) to the pressure rise ($P_{rise}$), as represented by reference numeral 148. An absorption coefficient (AC), based on the AR (formulas detailed below) can be calculated, as represented by reference numeral 159 in FIG. 4. As described above, the RH measurement (i.e., which gives $RH_{chamber}$) is used to determine a humidity error ($RH_{error}$) based on whether a desired humidity setpoint ($RH_{setpoint}$) has been achieved, i.e., $RH_{error}=RH_{setpoint}-RH_{chamber}$, as represented by the summing junction 172, its inputs 151 and 146, and its output 173. The next quantity of water to be injected (e.g., the injection time, $t_{inject}$, or the time the water inject valve 138 is open) can then be calculated based on the absorption coefficient (AC), which is based on the absorption ratio (AR), and the humidity error ($RH_{error}$). This is represented by reference numeral 160 in FIG. 4. The calculated amount of water is then injected—see item 153 in FIG. 4, and so on.

The advantage of using an internal state observer in the humidity control method is that it can be used to adjust the gain of the control (i.e., the water injector). Further, this is an unbiased estimate in that it is not affected by variations in the chamber configuration such as volume taken up by the load 105, or temperature (e.g., of the injections).

Figure 5:
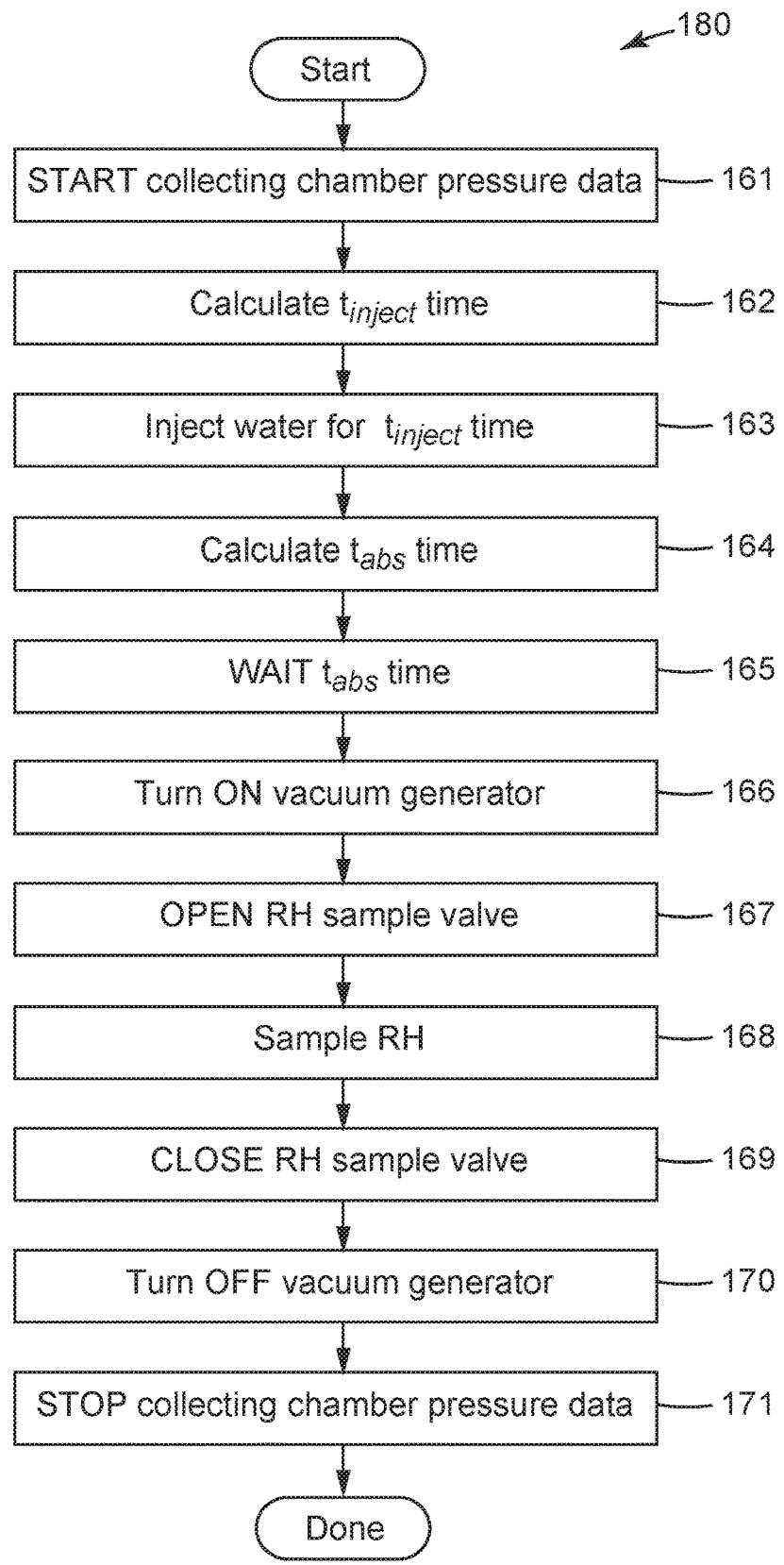
FIG. 5 is a flow chart representing the humidity control method of FIG. 4.
Figure 6A:
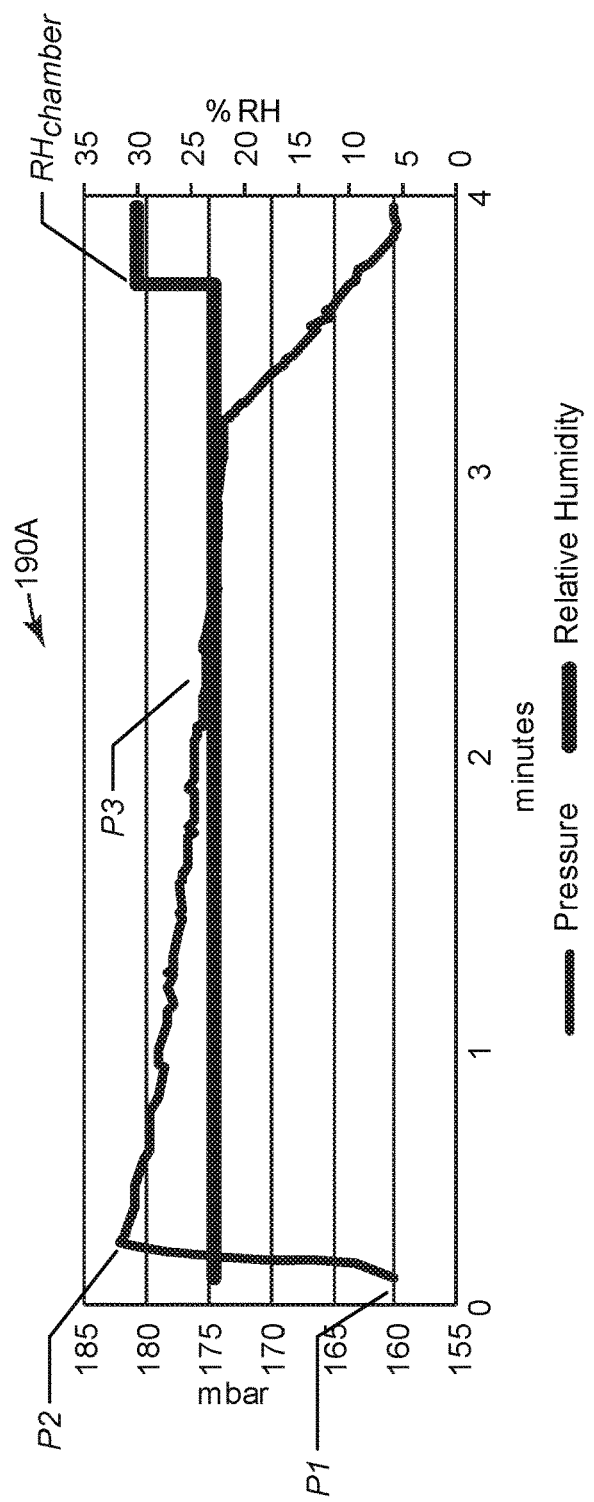
FIGS. 6A and 6B illustrate timing diagrams further representing the humidity control method represented in FIGS. 4 and 5.
Figure 6B:
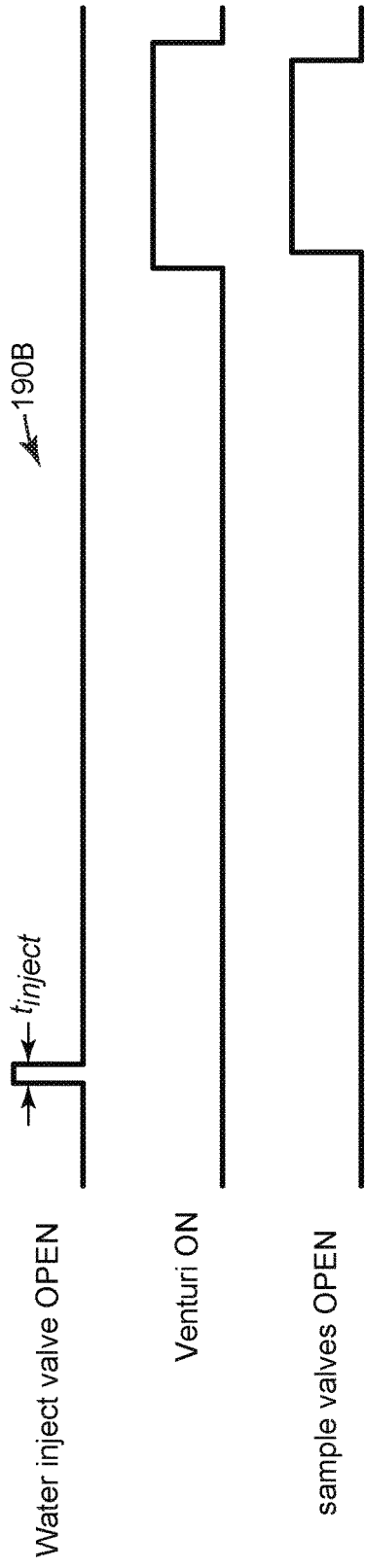

Additional details of the humidity control method are shown in FIGS. 5, 6A and 6B. FIGS. 3A-3C, described above, illustrate when the humidity control method is used by the humidification stage 20. FIG. 5 illustrates a detailed flow chart 180 for the humidity control method. As a result, the flow chart of FIG. 5 can be inserted into the overall humidification stage 20 of FIGS. 3A-3C for the humidity control method 66 of the humidification ramp-up phase 42 (see FIG. 3B) and the humidity control method 84 of the humidification hold phase 44 (see FIG. 3C). FIGS. 6A and 6B illustrate timing diagrams 190A and 190B, respectively, for the humidity control method.

Generally, at the start of the humidification stage 20 (i.e., at the humidification ramp-up phase 42, see FIG. 3A), the RH level in the chamber 102 is unknown. It will generally be low (e.g., 0 to 15% RH) at this point, because the chamber air was evacuated in the preceding air removal stage 16 (see FIG. 2). To ensure the RH level is known before injecting water vapor into the chamber 102, the first sequence in the humidity control method of the present disclosure generally does not perform an injection.

A consequence of not injecting at the start of ramp-up is that there is no pressure data to calculate an injection time. For this reason, the injection time ($t_{inject}$), or the length of time the water inject valve 138 is open for the first water injection in the humidification ramp-up phase 42 is a constant value that has been determined to be safe, independent of the state of the chamber 102.

Therefore, the first sequence generally does not perform an injection; next, a first fixed quantity of water is generally injected (e.g., the water inject valve 138 is opened for a fixed injection time ($t_{inject}$); and next, a second, calculated quantity of water is injected (e.g., the water inject valve 138 is opened for a calculated injection time ($t_{inject}$). This provides a customized humidity control method for each load.

A single humidity control sequence or cycle generally proceeds as follows:
 1. Start of sequence, start sampling chamber pressure (i.e., at time $t_o$)—see step 161 of FIG. 5.
 2. Calculate the injection time $t_{inject}$ for the water intake valve 138—see step 162 of FIG. 5 and items 157, 159 and 160 of FIG. 4:
  a. If this is the first injection in ramp-up, set inject time to preset constant value. In some embodiments, the constant inject time can range from about 5 to about 1000 milliseconds (msec), in some embodiments, from 50 to about 500 msec, and in some embodiments, from about 100 to 300 msec.
  b. Else, calculate injection time based on pressure measurements and humidity measurements from the previous sequence, where:
   $P_1$ is the chamber pressure prior to injecting water vapor into chamber 102;
   $P_2$ is the maximum chamber pressure detected after injecting water vapor into chamber; and
   $P_3$ is the average chamber pressure at to plus X minutes. This X-minute delay is also the minimum load absorption time allowed, and in some embodiments, can be about 2 minutes.

Using the three pressure values, calculate the absorption ratio (AR) as the ratio of pressure drop ($P_{drop}$) to pressure rise ($P_{rise}$) (i.e., $P_{drop}/P_{rise}$), where $P_{drop}=P_2-P_3$ and $P_{rise}=P_2-P_1$:

$$AR=(P_2-P_3)(P_2-P_1)$$

The AR will tend to be negative for non-absorbent loads and positive for absorbent loads. With reference to FIG. 6A, the pressure curve would be shown as increasing from $P_2$ to $P_3$ in non-absorbent loads. As a result, the injection cycle shown in FIGS. 6A and 6B pertains to an absorbent load, because the pressure curve is shown as decreasing from $P_2$ to $P_3$ and therefore having a positive $P_{drop}$.

Calculate the absorption coefficient (AC), based on AR:

$$AC=1+(P_{gain,AR}*AR),$$

where $P_{gain,AR}$ is a proportional gain constant, e.g., used to scale the absorption ratio (AR) based on the target chamber temperature (e.g., for a given sterilization cycle). In some embodiments, $P_{gain,AR}$ can range from about 0.1 to about 10, in some embodiments, from about 1 to about 10, in some embodiments, from about 2 to about 8, in some embodiments, from about 4 to about 6, and in some embodiments, can be about 5.

Use AC and the humidity error ($RH_{error}$) to calculate the injection time (i.e., the time the water inject valve 138 is open) for the next water injection:

$$RH_{error}=RH_{setpoint}-RH_{chamber}$$

$$t_{inject}=P_{gain}*AC*RH_{error}, \text{ where}$$

$P_{gain}$ is a proportional gain constant, e.g., used to scale the chamber humidity error ($RH_{error}$) based on the target chamber temperature for the sterilization cycle. In some embodiments, $P_{gain}$ can range from about 1 to about 100, in some embodiments, from about 10 to about 100, in some embodiments, from about 25 to about 100, and in some embodiments, from about 50 to about 100.

Set $t_{inject}$ to be greater than zero and less than an upper limit of time to avoid injecting too much water vapor into the chamber 102.

Based on the calculations shown above, the injection time ($t_{inject}$) is ratiometric in pressure. Since relative humidity is a direct function of pressure, the present inventors discovered that improved humidification control and efficiency could be achieved when such an absorption observer (see absorption estimator 158 in FIG. 4) is used to estimate the internal state of the humidification stage 20.

3. Open water inject valve 138 for $t_{inject}$ amount of time—see step 163 of FIG. 5 and item 153 of FIG. 4. The water injection generally results in a pressure rise in the chamber 102, followed by a pressure drop as the load 105 (if present) absorbs at least some of the water vapor.

4. Calculate load absorption $t_{abs}$—see step 164 of FIG. 5:
  a. If in humidification ramp-up phase 42 (see FIGS. 3A and 3B), set the load absorption time $t_{abs}$ to a constant value. In some embodiments, the constant load absorption time can range from about 100 to about 200 seconds, and in some embodiments, from about 120 to about 180 seconds.
  b. If in humidification hold phase 44 (see FIG. 3C), use the AC to scale the load absorption time:

$$t_{abs} = t_{abs,h,max}/AC, \text{ where}$$

$t_{abs,h,max}$ represents the maximum absorption time, which is a constant value that can be preset for a specific application. In some embodiments, $t_{abs,h,max}$ can range from about 100 to about 1000 seconds, in some embodiments, from about 120 to about 1000 seconds, in some embodiments, from about 200 to about 1000 seconds, and in some embodiments, can be about 360 seconds.

Set $t_{abs}$ to be greater than zero (i.e., so that there is sufficient time for the load to absorb water) and less than an upper limit of time (i.e., to ensure that multiple inject and measure RH sequences can be performed during the humidification hold phase 44).

5. Wait $t_{abs}$ amount of time—see step 165 of FIG. 5.
6. Turn On Vacuum Generator—see step 166 of FIG. 5.
7. Open RH sample valves 126, 128—see step 167 of FIG. 5. In some embodiments, there can be a slight delay or lag between the opening of the valves 126 and 128. For example, in some embodiments, the first RH sample valve 126 can be opened slightly before the second RH sample valve 128 is opened.
8. Sample RH—see step 168 of FIG. 5 and item 154 of FIG. 4. That is, a sample of the gaseous environment from within the chamber 102 is drawn through branch line 122 and manifold 127, as described above, to position the sample in contact with the humidity sensor 124 to sense the humidity of the sample. This arrangement is shown by way of example only, and it should be understood that in some embodiments, the humidity sensor 124 can instead be positioned in constant fluid communication with the chamber 102, or directly located within the chamber 102.
9. Close RH sample valves 126, 128—see step 169 of FIG. 5. Similar to opening the RH sample valves 126, 128, in some embodiments, there can be a slight delay or lag between the closing of each of the valves 126 and 128.
10. Turn off vacuum generator—see step 170 of FIG. 5. For example, for the sterilizer 100 of FIG. 1, this would include turning on the vacuum pump valve 110 and the venturi 116.

As shown in the control diagram 150 of FIG. 4, the humidity control method can then be repeated for a subsequent water injection, i.e., to inject a second quantity of water into the chamber 102, a third quantity of water into the chamber 102, and so on, as further shown by line 69 in the humidification ramp-up phase 42 of FIGS. 3A and 3B and line 89 of the humidification hold phase 44 of FIG. 3C. That is, the above steps can be repeated to cause a new water injection until humidification is complete, i.e., until $RH_{setpoint}$ has been reached and held for the predetermined hold time (see step 82 of FIG. 3C).

11. When the process is complete, stop collecting chamber pressure data—see step 171 of FIG. 5.

As can be seen from the above-described cycle, a first quantity of water can be injected into the chamber 102, and then pressure measurements and humidity measurements from that first injection can be measured; an absorption ratio (AR) can be calculated; an absorption coefficient (AC) can be calculated; a humidity error ($RH_{error}$) can be calculated; and these values can be used to calculate an injection time for a second water injection. That is, the second quantity of water to be injected (e.g., as water vapor) into the chamber 102 is proportional to the absorption coefficient (AC) and the humidity error ($RH_{error}$). The cycle can be repeated for a third water injection, and so on. In some embodiments, as shown in FIGS. 3A-3C, the cycle can be repeated during a humidification ramp-up phase (e.g., phase 42 of FIGS. 3A and 3B) until $RH_{chamber}$ reaches or exceeds $RH_{setpoint}$, after which the humidification stage can transition to a humidification hold phase (e.g., phase 44 of FIG. 3C), which can be maintained for a desired hold period.

With continued reference to FIGS. 6A and 6B, a single water injection cycle is represented. FIGS. 6A and 6B are aligned along the same x-axis, which represents time (i.e., in minutes). FIG. 6A represents pressure and RH measurement of the chamber 102 for the water injection cycle. As shown, $P_1$ is taken before water is injected at to (i.e., before the water inject valve 138 is opened—see the first line in FIG. 6B). The "Water inject valve OPEN" line in FIG. 6B represents an exemplary length of time in which the water inject valve 138 is open during a water injection cycle. The injection time $t_{inject}$ can be defined as the width (i.e., x-component) of the step curve shown in the "Water inject valve OPEN" line.

As further shown by comparing the first line of FIG. 6B and FIG. 6A, the water injection results in a pressure rise in the chamber 102, and the pressure peaks at pressure $P_2$ resulting in a pressure rise ($P_{rise}$) equal to $P_2-P_1$. $P_3$ is further illustrated in FIG. 6A as being the pressure at a timepoint equal to $P_1$ plus X minutes. X is set to about 2 minutes in the injection cycle shown in FIGS. 6A and 6B. As described above, the pressure drop ($P_{drop}$; i.e., $P_2-P_3$) for this injection cycle is positive, representing an absorbent load. The pressure drop ($P_{drop}$) is generally proportional to load size.

The relative humidity line in FIG. 6A shows a constant humidity for the first part of the injection cycle. This is by way of example only, because using the sterilizer 100 of FIG. 1, the humidity measurements are taken by removing a sample from the chamber 102. As such, relative humidity is measured according to a "sample and hold" process. Thus, the constant value (e.g., about 23% RH) shown for the first part of the cycle of FIG. 6A represents the relative humidity measured in the previous injection cycle for the given injection cycle illustrated in FIGS. 6A and 6B.

As described above, following injection, the load 105 will be allowed to absorb the water injected for a load absorption time ($t_{abs}$). If the water injection cycle is during humidification ramp-up, this will be a constant value, and if the water injection cycle is during humidification hold, this will be a calculated value, based on AC. After the load absorption time has passed, a vacuum generator will be turned on (see step 166 of FIG. 5; e.g., the vacuum pump valve 110 and the venturi 116), as shown in the second "Venturi ON" line of FIG. 6B. Then, the humidity can be sensed (e.g., by the RH sensor 124 when RH sample valves 126, 128 are open), as shown by the third "RH sample valves OPEN" line of FIG. 6B. As further shown by this line, the RH sample valves are closed just before the vacuum generator is turned off (see also steps 169 and 170 of FIG. 5).

As shown in FIG. 6A, the relative humidity line increases based on the humidity sensed by the humidity sensor (e.g., the humidity sensor 124). The new relative humidity value $RH_{chamber}$ (e.g., about 30% RH in FIG. 6A) is then compared to the desired humidity level ($RH_{setpoint}$) to determine the humidity error ($RH_{error}$), as described above. If $RH_{error}$ has met or exceeded $RH_{setpoint}$, the humidification switches to the humidification hold mode (see the humidification hold phase 44 of FIG. 3C), otherwise, the humidification remains in humidification ramp-up mode (see the humidification ramp-up phase 42 of FIGS. 3A and 3B). After the first time the humidity in the chamber ($RH_{chamber}$) meets or exceeds $RH_{setpoint}$, the humidification hold phase 44 can be initiated.

The humidity control systems and methods disclosed herein are generally described with respect to the sterilizer 100 of FIG. 1 and a sterilization process (e.g., the sterilization method 10 of FIG. 2) by way of example only. However, it should be understood that the humidity control systems and methods could instead be employed with other sterilizer configurations and sterilization processes, respectively. In addition, as mentioned above, the humidity control systems and methods of the present disclosure can also be employed in non-sterilizing systems, devices and processes.

The following embodiments are intended to be illustrative of the present disclosure and not limiting.

EMBODIMENTS

1. A method for controlling humidity, the method comprising:
providing a chamber configured to receive objects to be sterilized;
injecting a first quantity of water into the chamber as water vapor;
determining a pressure rise and a pressure drop in the chamber resulting from injecting a first quantity of water into the chamber;
calculating an absorption ratio (AR) as the ratio of the pressure drop to the pressure rise;
sensing the humidity of the chamber after injecting a first quantity of water to determine a first humidity value ($RH_{chamber}$);
comparing the first humidity value to a pre-selected humidity value ($RH_{setpoint}$) to determine a humidity error ($RH_{error}$), wherein $RH_{error}=RH_{setpoint}-RH_{chamber}$; and
injecting a second quantity of water into the chamber as water vapor, wherein the second quantity of water is calculated based on the absorption ratio (AR) and the humidity error ($RH_{error}$).

2. The method of embodiment 1, wherein $RH_{setpoint}$ ranges from 20 to 80% relative humidity.

3. The method of embodiment 1 or 2, further comprising positioning a load of objects to be sterilized within the chamber and sealing the chamber.

4. The method of embodiment 3, wherein positioning a load of objects to be sterilized within the chamber and sealing the chamber occurs prior to injecting a first quantity of water into the chamber.

5. The method of any of embodiments 1-4, further comprising drawing a vacuum within the chamber prior to injecting a first quantity of water into the chamber.

6. The method of any of embodiments 1-5, further comprising heating the chamber to a predetermined temperature prior to injecting a first quantity of water into the chamber.

7. The method of any of embodiments 1-6, further comprising calculating an absorption coefficient (AC), wherein $AC=1+(P_{gain,AR}*AR)$, where $P_{gain,AR}$ is a proportional gain constant, and wherein the second quantity of water is calculated based on the absorption coefficient (AC) and the humidity error ($RH_{error}$).

8. The method of embodiment 7, wherein the proportional gain constant ($P_{gain,AR}$) ranges from about 0.1 to about 10.

9. The method of embodiment 7 or 8, wherein the second quantity of water is proportional to the absorption coefficient (AC) and the humidity error ($RH_{error}$).

10. The method of any of embodiments 1-9, wherein injecting a first quantity of water or a second quantity of water into the chamber as water vapor includes opening a water inject valve for an injection time ($t_{inject}$).

11. The method of embodiment 10, wherein the injection time ($t_{inject}$) is a constant value.

12. The method of embodiment 11, wherein the injection time ($t_{inject}$) ranges from 5 to 1000 milliseconds.

13. The method of embodiment 10, wherein $t_{inject}=P_{gain}*AC*RH_{error}$, where $P_{gain}$ is a proportional gain constant used to scale the humidity error ($RH_{error}$).

14. The method of embodiment 13, wherein the proportional gain constant ($P_{gain}$) ranges from 1 to 100.

15. The method of any of embodiments 1-14, further comprising waiting for a load absorption time $t_{abs}$ after injecting a first quantity of water and before sensing the humidity of the chamber.

16. The method of embodiment 15, wherein the load absorption time ($t_{abs}$) is a constant value.

17. The method of embodiment 15, further comprising:
calculating an absorption coefficient (AC), wherein $AC=1+(P_{gain,AR}*AR)$, where $P_{gain,AR}$ is a proportional gain constant used to scale AR; and
calculating the load absorption time $t_{abs}$ as $t_{abs}=t_{abs,h,max}/AC$, where $t_{abs,h,max}$ is a constant representing a maximum load absorption time.

18. The method of embodiment 17, wherein the maximum load absorption time ($t_{abs,h,max}$) ranges from 120 to 1000 seconds.

19. The method of any of embodiments 1-18, further comprising:
providing a pressure sensor in fluid communication with the chamber; and
using the pressure sensor to determine the pressure rise and the pressure drop resulting from injecting a first quantity of water into the chamber.

20. The method of any of embodiments 1-19, further comprising:
providing a humidity sensor in selective fluid communication with the chamber by a valve; and
opening the valve to provide fluid communication between the humidity sensor and the chamber prior to sensing the humidity of the chamber.

21. The method of embodiment 20, wherein the humidity sensor is located in a humidity manifold, and wherein the valve is located between the chamber and the humidity manifold.

22. The method of embodiment 21, wherein the valve is a first valve, and further comprising:
providing a second valve located between the humidity manifold and a vacuum control system, wherein opening the valve to provide fluid communication between the humidity sensor and the chamber includes opening the first valve and the second valve to draw a portion of the gaseous environment within the chamber into the humidity manifold; and
closing the first valve and the second valve.

23. The method of embodiment 22, wherein closing the first valve and the second valve occurs prior to injecting a second quantity of water into the chamber.

24. The method of any of embodiments 1-23, further comprising:

determining a second pressure rise and a second pressure drop in the chamber resulting from injecting a second quantity of water into the chamber;

calculating a second absorption ratio ($AR_2$) as the ratio of the second pressure drop to the second pressure rise;

sensing the humidity of the chamber after injecting a second quantity of water to determine a second humidity value ($RH_{chamber,2}$);

comparing the second humidity value to a pre-selected humidity value ($RH_{setpoint}$) to determine a second humidity error ($RH_{error,2}$), wherein $RH_{error,2}=RH_{setpoint}-RH_{chamber,2}$; and injecting a third quantity of water into the chamber as water vapor, wherein the third quantity of water is calculated based on the second absorption ratio ($AR_2$) and the second humidity error ($RH_{error,2}$).

25. The method of any of embodiments 1-24, further comprising releasing the biocidal gas within the chamber.

26. A sterilizer for sterilizing objects with biocidal gas, the sterilizer comprising:

a chamber for receiving objects to be sterilized;

a biocidal gas control system which can be connected to a biocidal gas source for controlling the release of biocidal gas into the chamber; and a humidity control system for manipulating the gaseous environment within the chamber, the humidity control system comprising:

a water control system which can be connected to a water source for injecting a selectable quantity of water into the chamber;

a pressure sensor in fluid communication with the chamber for measuring pressure in the chamber;

a humidity sensor in fluid communication, or in selective fluid communication, with the chamber for sensing a humidity value ($RH_{chamber}$) of the gaseous environment in the chamber; and a controller configured to:

determine a pressure drop and a pressure rise in the chamber resulting from a first quantity of water injected into the chamber, calculate an absorption ratio (AR) as the ratio of the pressure drop to the pressure rise, compare the humidity value ($RH_{chamber}$) to a pre-selected humidity value ($RH_{setpoint}$) to determine a humidity error ($RH_{error}$), wherein $RH_{error}=RH_{setpoint}-RH_{chamber}$, and determine a second quantity of water to be injected into the chamber based on the absorption ratio (AR) and the humidity error ($RH_{error}$).

27. A humidity control system for manipulating the gaseous environment within a chamber, the system comprising:

a water control system which can be connected to a water source for injecting a selectable quantity of water into the chamber;

a pressure sensor in fluid communication with the chamber for measuring pressure in the chamber;

a humidity sensor in fluid communication, or in selective fluid communication, with the chamber for sensing a humidity value ($RH_{chamber}$) of the gaseous environment in the chamber; and a controller configured to:

determine a pressure drop and a pressure rise in the chamber resulting from a first quantity of water injected into the chamber, calculate an absorption ratio (AR) as the ratio of the pressure drop to the pressure rise, compare the humidity value ($RH_{chamber}$) to a pre-selected humidity value ($RH_{setpoint}$) to determine a humidity error ($RH_{error}$), wherein $RH_{error}=RH_{setpoint}-RH_{chamber}$, and determine a second quantity of water to be injected into the chamber based on the absorption ratio (AR) and the humidity error ($RH_{error}$).

28. The sterilizer of embodiment 26, wherein the humidity control system further includes a vacuum control system comprising a vacuum source for evacuating the chamber and a vacuum line in fluid communication with the chamber.

29. The system of embodiment 27, further comprising a vacuum control system comprising a vacuum source for evacuating the chamber and a vacuum line in fluid communication with the chamber.

30. The sterilizer of embodiment 26 or 28 or the system of embodiment 27 or 29, wherein the second quantity of water is further based on an absorption coefficient (AC), wherein $AC=1+(P_{gain,AR}*AR)$, where $P_{gain,AR}$ is a proportional gain constant used to scale AR, and wherein the second quantity of water is calculated based on the absorption coefficient (AC) and the humidity error ($RH_{error}$).

31. The sterilizer of embodiment 26, 28 or 30 or the system of embodiment 27, 29 or 30, wherein the water control system is configured to inject a selectable quantity of water into the chamber by opening a water inject valve for an injection time ($t_{inject}$).

32. The sterilizer or system of embodiment 31, wherein the injection time ($t_{inject}$) is a constant value.

33. The sterilizer or system of embodiment 31, wherein the injection time ($t_{inject}$)=$P_{gain}*AC*RH_{error}$, where $P_{gain}$ is a proportional gain constant used to scale the humidity error ($RH_{error}$).

34. The sterilizer of any of embodiments 26, 28 and 30-33 or the system of any of embodiments 27 and 29-33, wherein the humidity value is a first humidity value, and wherein the humidity sensor is further configured to sense a second humidity value of the gaseous environment in the chamber.

35. The sterilizer or system of embodiment 34, wherein the controller is further configured to:

determine a second pressure rise and a second pressure drop in the chamber resulting from injecting a second quantity of water into the chamber;

calculate a second absorption ratio ($AR_2$) as the ratio of the second pressure drop to the second pressure rise;

sense the humidity of the chamber after injecting a second quantity of water to determine a second humidity value ($RH_{chamber,2}$);

comparing the second humidity value ($RH_{chamber,2}$) to a pre-selected humidity value ($RH_{setpoint}$) to determine a second humidity error ($RH_{error,2}$), wherein $RH_{error,2}=RH_{setpoint}-RH_{chamber,2}$; and determine a third quantity of water to be injected into the chamber based on the second absorption ratio ($AR_2$) and the second humidity error ($RH_{error,2}$).

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure.

All references and publications cited herein are expressly incorporated herein by reference in their entirety into this disclosure.

Various features and aspects of the present disclosure are set forth in the following claims.

What is claimed is:

1. A sterilizer for sterilizing objects comprising:
a chamber for receiving objects to be sterilized;
a humidity control system comprising:
a water control system which can be connected to a water source for injecting a first quantity of water vapor into the chamber;
a pressure sensor in fluid communication with the chamber for measuring pressure in the chamber;
a humidity sensor in fluid communication, or in selective fluid communication, with the chamber for sensing a first humidity value ($RH_{chamber}$) of the first quantity of water vapor in the chamber; and
a controller configured to inject a second quantity of water vapor into the chamber, wherein the controller is configured to:
determine a pressure drop and a pressure rise in the chamber resulting from the first quantity of water vapor injected into the chamber,
calculate an absorption ratio (AR) as the ratio of the pressure drop to the pressure rise,
compare the first humidity value ($RH_{chamber}$) to a pre-selected humidity value ($RH_{setpoint}$) to determine a humidity error ($RH_{error}$), wherein $RH_{error} = RH_{setpoint} - RH_{chamber}$, and
determine a second quantity of water vapor to be injected into the chamber based on the absorption ration (AR) and the humidity error ($RH_{error}$).

2. The sterilizer of claim 1, wherein the controller is configured to calculate an absorption coefficient (AC), wherein $AC = 1 + (P_{gain,AR} * AR)$, where $P_{gain,AR}$ is a proportional gain constant, and wherein the second quantity of water vapor is calculated based on the absorption coefficient (AC) and the humidity error ($RH_{error}$).

3. The sterilizer of claim 2, wherein the second quantity of water vapor is proportional to the absorption coefficient (AC) and the humidity error ($RH_{error}$).

4. The sterilizer of claim 1, further comprising a water injection valve for injecting the first quantity of water vapor or second quantity of water vapor.

5. The sterilizer of claim 4, further comprising a timer measuring an injection time ($t_{inject}$) of the water injection value.

6. The sterilizer of claim 5, wherein the injection time ($t_{inject}$) is a constant value.

7. The sterilizer of claim 6, wherein the injection time ($t_{inject}$) = $P_{gain} * AC * RH_{error}$, where $P_{gain}$ is a proportional gain constant used to scale the humidity error ($RH_{error}$).

8. The sterilizer of claim 1, further comprising a RH sample valve.

9. The sterilizer of claim 8, wherein the humidity sensor is located in a humidity manifold, and wherein the RH sample valve is located between the chamber and the humidity manifold.

10. The sterilizer of claim 1, further comprising objects to be sterilized within the chamber and sealing the chamber.

11. The sterilizer of claim 1, further comprising a biocidal gas control system which can be connected to a biocidal gas source for controlling the release of biocidal gas into the chamber.

* * * * *

UNITED STATES PATENT AND TRADEMARK OFFICE
CERTIFICATE OF CORRECTION

PATENT NO. : 10,967,087 B2
APPLICATION NO. : 16/160412
DATED : April 6, 2021
INVENTOR(S) : Goetz et al.

Page 1 of 1

It is certified that error appears in the above-identified patent and that said Letters Patent is hereby corrected as shown below:

In the Specification

Column 8
Line 26, Delete "unduely" and insert -- unduly --, therefor.

In the Claims

Column 21
Line 30, In Claim 1, delete "ration" and insert -- ratio --, therefor.

Signed and Sealed this
Fourteenth Day of September, 2021

Drew Hirshfeld
*Performing the Functions and Duties of the*
*Under Secretary of Commerce for Intellectual Property and*
*Director of the United States Patent and Trademark Office*